(12) United States Patent
Haeussinger

(10) Patent No.: US 9,901,368 B2
(45) Date of Patent: Feb. 27, 2018

(54) POINT SPECIFIC JUNCTIONAL TOURNIQUET

(71) Applicant: John D. Haeussinger, Santee, CA (US)

(72) Inventor: John D. Haeussinger, Santee, CA (US)

( * ) Notice: Subject to any disclaimer, the term of this patent is extended or adjusted under 35 U.S.C. 154(b) by 0 days.

(21) Appl. No.: 15/403,149

(22) Filed: Jan. 10, 2017

(65) Prior Publication Data
US 2017/0196569 A1 Jul. 13, 2017

Related U.S. Application Data

(60) Provisional application No. 62/276,944, filed on Jan. 10, 2016.

(51) Int. Cl.
*A61B 17/132* (2006.01)
*A61B 17/3215* (2006.01)
*A61B 17/00* (2006.01)

(52) U.S. Cl.
CPC ...... *A61B 17/3215* (2013.01); *A61B 17/1327* (2013.01); *A61B 17/1322* (2013.01); *A61B 2017/00526* (2013.01)

(58) Field of Classification Search
CPC .............. A61B 17/132; A61B 17/1322; A61B 17/1325; A61B 17/1327
See application file for complete search history.

(56) References Cited

U.S. PATENT DOCUMENTS

| 1,771,689 | A | * | 7/1930 | Owen | A61B 17/1327 606/203 |
|---|---|---|---|---|---|
| 5,207,303 | A | * | 5/1993 | Oswalt | A45C 13/02 190/108 |
| 8,834,517 | B2 | * | 9/2014 | Croushorn | A61B 17/1325 606/203 |
| 2005/0049630 | A1 | * | 3/2005 | Ambach | A61B 17/1327 606/203 |
| 2013/0041303 | A1 | * | 2/2013 | Hopman | A61B 17/1322 602/23 |
| 2013/0267994 | A1 | * | 10/2013 | Crowder | A61B 17/1325 606/203 |

\* cited by examiner

*Primary Examiner* — Diane Yabut
(74) *Attorney, Agent, or Firm* — Richard D. Clarke

(57) ABSTRACT

The present invention is directed to a Point Specific Junctional Tourniquet Kit designed for the treatment of hemorrhage control of junctional injuries to a patient's torso especially in the area of the iliac (hip/groin area) and axillary (shoulder/armpit area) arteries where blood flow is extremely hard to stop. The complete kit contains a variety of components to give caregivers in the military as well as civilian medical caregivers a means for treating a wide variety of severe injuries, in the pre-ambulance environment, increasing the chances of a victim surviving and reaching a higher level of care.

20 Claims, 7 Drawing Sheets

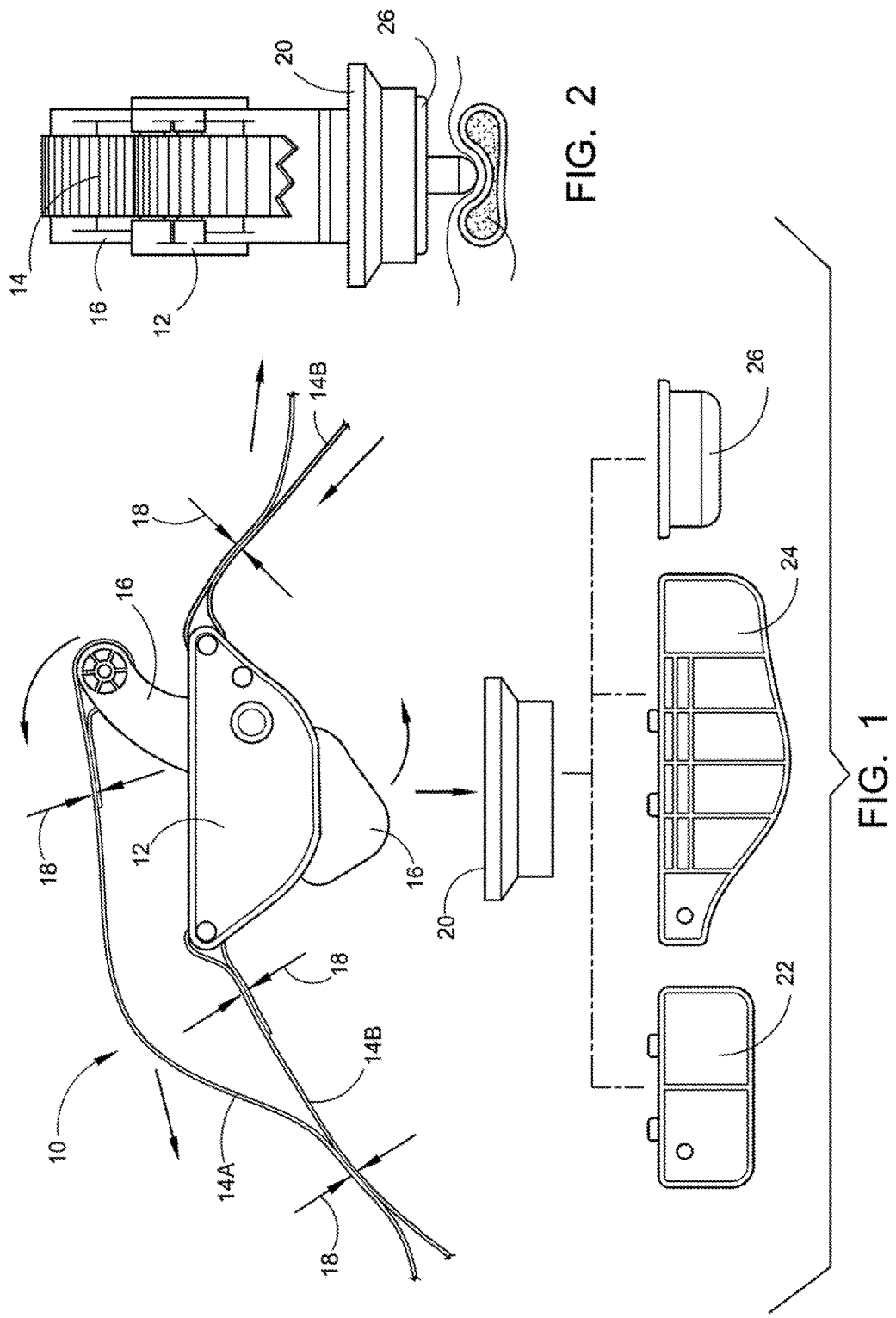

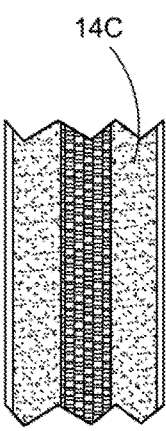 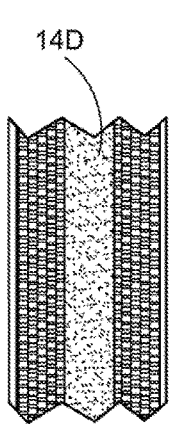 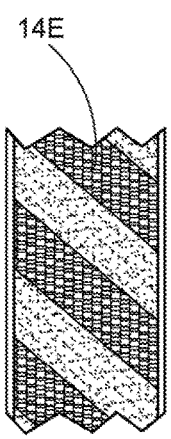 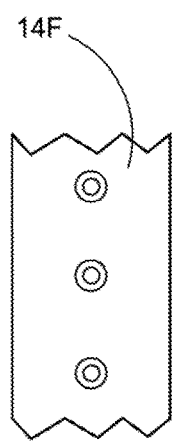
FIG. 8　　FIG. 9　　FIG. 10　　FIG. 11
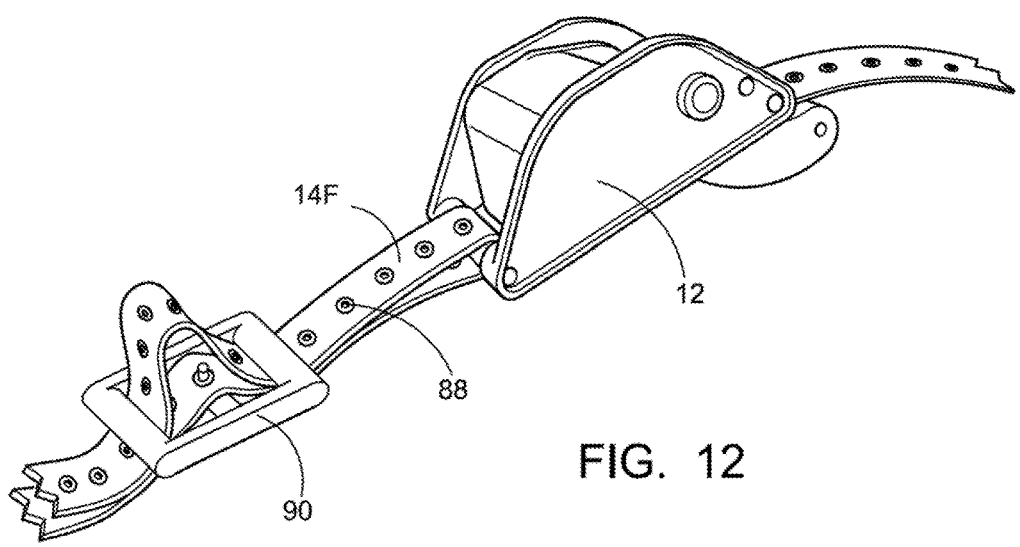
FIG. 12

POINT SPECIFIC JUNCTIONAL TOURNIQUET

FIELD OF THE INVENTION

This invention relates to a tourniquet kit dealing with wounds involving uncontrolled hemorrhaging from the iliac, axillary and other major arteries of the body.

BACKGROUND OF THE INVENTION

Various tourniquet devices that use a wide variety of clamping and/or pneumatic means to apply pressure to various limbs on the body have been attempted. However, prior attempts at occluding hemorrhaging from these major blood vessels of the body have not been completely successful, especially if attempted on gross battle-field wounds such as leg amputations due to anti-personnel mines or high velocity bullet percussion wounds to the lower extremities and other injuries associated with improvised explosive device (IED) detonations and the like.

This is an article where the USAMRMC is seeking information regarding novel junctional tourniquets, Junctional Tourniquets for the Department of Defense Research, on Combat Casualty Care The Combat Casualty Care Research Program of the Medical Research and Materiel Command (USAMRMC) provides integrated capabilities for far-forward medical care to reduce the mortality and morbidity associated with major battlefield wounds and injuries. The primary focus is to make possible the highest degree of medical care available in the pre-ambulance and pre-evacuation environment prior to reaching a higher level of care. The USAMRMC is seeking information regarding novel junctional tourniquets, both FDA approved and prototype devices, for hemorrhage control of junctional injuries and quadrant injuries on the battlefield including iliac and axillary. Interested firms should submit a 1 to 3 page white paper (with additional sheets for diagrams as necessary) describing such devices and the concept of use. Information will be reviewed pursuant to consideration for the development of a request for devices to be tested. As such, any descriptions of clinical use or test and evaluation studies will be of use. For the purposes of this request for information, we anticipate that devices: Will be able to occlude arterial bleeding from femoral, iliac, subclavian, axillary, and brachial arteries at compressible sites where standard tourniquets cannot be applied;
  1. Can be applied easily in a tactical environment;
  2. Must not slip during tightening or following application;
  3. Be capable of easy release and reapplication;
  4. Be of light weight;
  5. Have long shelf life, low cost and low cube.

While developing a Junctional Tourniquet Kit and protocol, for rural and urban law enforcement personnel, it was discovered that no practical torso tourniquets were available. To rectify the situation the Junctional Tourniquet Kit was devised, and created, that addresses, and satisfies, all of USAMRMC's "junctional tourniquet" requirements plus being a great advancement in first aide care for military as well as the civilian medical caregivers.

Numerous innovations for tourniquets have been provided in the prior art that art described as follows. Even though these innovations may be suitable for the specific individual purposes to which they address, they differ from the present Junctional Tourniquet Kit as hereinafter contrasted. The following is a summary of those prior art patents most relevant to the design at hand, as well as a description outlining the difference between the features of the present Junctional Tourniquet Kit and those of the prior art.

U.S. Pat. No. 6,884,254 of Shan L. Brooks describes a tourniquet system having a strap, a clamp for selectively engaging the strap in which once the clamp engages the strap, the clamp permits the strap to pass substantially freely in a direction away from the clamp and substantially prevents the strap from passing in a direction towards the clamp and securing structure attached to the strap for securing the strap.

This patent describes a tourniquet system having a strap that may be useful around the legs and arms, but would be of no use on the major arteries of the torso.

U.S. Pat. No. 8,834,517 of Croushorn et al. describes a portable pneumatic abdominal aortic tourniquet for occlusion of the abdominal descending aorta to restrict blood supply to a non-compressible arterial hemorrhage in the abdominal region. The tourniquet comprising an adjustable waist strap for securing around an abdomen; a directed air bladder mounted to the waist strap having a generally "V" shaped construction operable between a deflated condition wherein the directed air bladder is collapsed, and an inflated condition wherein the directed air bladder is expanded for exerting pressure against the abdomen; and, an air source connected to the directed air bladder for operating the directed air bladder between the deflated condition and the inflated condition. This device is not suited for application on the upper torso or subclavian area.

This patent describes a portable pneumatic abdominal aortic tourniquet for occlusion of the abdominal descending aorta with arterial hemorrhage in the abdominal region. This patent does not supply a kit with items that will be useful in a variety of different areas of the body. Within this device also exists the possibility of a fatal flaw, in that this device is made from rubber or the like. As rubber and some similar materials age they can become brittle and susceptible to cracking, leaking and breaking.

U.S. Pat. No. 9,149,280 of Croushorn et al. describes a portable pneumatic abdominal aortic tourniquet for occlusion of the abdominal descending aorta to restrict blood supply to a non-compressible arterial hemorrhage in or below the inguinal region is presented. The tourniquet includes an adjustable waist strap for securing it around the abdomen of a patient and a windlass rod connected to the waist strap to selectively tighten the strap as needed to tightly secure it to patient. A directed air bladder is mounted to the waist strap having a generally "V" shaped construction and is expanded for exerting directed pressure against the abdomen. Upon inflation of the air bladder and adjustment of the windlass, occlusion or restriction of blood flow through the abdominal descending aorta will occur which will achieve cessation of hemorrhage in or below the inguinal area or achieve other therapeutic effects like elevated blood pressure to enhance CPR or blood flow control to the lower extremities.

This patent still does not supply a kit with items that will be useful in a variety of different areas of the body to restrict blood flow.

US pending Patent Application Publication No. 20070005107 of John Janota describes a military emergency tourniquet is a device for rapidly and easily reducing or stopping blood flow to a limb. The tourniquet utilizes a closed loop system and includes a twistable strap, a base including two opposing entry apertures and an exit aperture, a windlass and at least one receiving loop. The twistable strap is slidably positioned through the opposing entry apertures and the exit aperture thereby forming a closed loop. The windlass is positioned outside of the closed loop and is affixed to one end of the strap. The windlass includes an aperture capable of sliding the opposing end of the strap there through. The receiving loop receives an end of the windlass and is affixed to the base. This device would require a substantial length of limb to be protruding from torso to function. Therefore, it would be of no use in cases of complete limb amputations.

This patent describes a military emergency tourniquet is a device for rapidly and easily reducing or stopping blood flow to a limb. The tourniquet utilizes a closed loop system and includes a twistable strap but does not supply a kit suitable for application on various parts of the body including the torso. Thus, as mentioned, a disadvantage of this device would be that it would be of no use in cases involving complete amputations.

US pending Patent Application Publication No. 20130267994AL of Tyler L. Crowder describes an occlusion attachment device for coupling with a tourniquet includes a projection that can be attached using a platform to a portion of a tourniquet in an emergency situation, thereby providing a modified tourniquet that includes the projection. Clip-on, slide-on, and clamping structures associated with the platform are described.

This patent describes an occlusion attachment device for coupling with a tourniquet suitable for an arm or a leg but does not supply a Junctional Tourniquet Kit suitable for application on various parts of the body including the torso.

U.S. Pat. No. 8,888,807 of Mark Esposito describes a tourniquet for restricting a flow of blood in a body part is presented. In accordance with embodiments of the present invention, the tourniquet comprises a first elongated member, and a second elongated member in slidable engagement with the first elongated member. In addition, the tourniquet includes a tensioning mechanism connected to the second elongated member, wherein a compressive force is applied to the body part upon applying a tensile force to the second elongated member using the tensioning mechanism. The tourniquet is suited for emergency use, and may be applied by using only one hand. Thus, the tourniquet may be applied, manipulated and tightened by the wearer, even if the wearer is limited to the use of a single hand.

This patent describes a tourniquet for restricting a flow of blood in a leg or arm but does not does not supply a kit with items that will be useful in a variety of different areas of the body, but would be of no use in complete dis-memberments.

U.S. Pat. No. 8,926,536 of Lance David Hopman et al describes a junctional and truncal tourniquet and a hip-girdling pelvic sling device for maintaining a desired amount of tension surrounding a person's hips and pelvis to securely support and stabilize a pelvis that has been fractured and for securing a pressure applying device to a person with a preferred amount of tension so that blood vessel-occluding pressure can be applied. Areas of mating types of fastener material such as mating hook-bearing fastener material and loop pile fastener material are arranged on the device to enable a strap to be secured at various effective lengths to provide a wide range of adjustability. The device may include inflatable bladders, and may be wrapped around a patient's torso to occlude blood vessels proximal to an injury on a limb. A bladder may be expandable in distinct tiers and may carry a separate and removable pressure-concentrating fitting. An auxiliary strap may be included and may be used to keep the junctional and truncal tourniquet in place on a patient's torso. This device also requires an existing limb be present to function.

This patent describes a junctional and truncal tourniquet and a hip-girdling pelvic sling device for maintaining a desired amount of tension surrounding a person's hips and pelvis to securely support and stabilize a pelvis that has been fractured but does not supply a tourniquet kit with items that will be useful in a variety of different areas of the body to restrict blood flow.

SUMMARY OF THE INVENTION

In this respect, before explaining at least one embodiment of the Junctional Tourniquet Kit in detail it is to be understood that it is not limited in its application to the details of construction and to the arrangement of the components set forth in the following description or illustrated in the drawings. The Junctional Tourniquet Kit is capable of other embodiments and of being practiced and carried out in various ways. Also, it is to be understood that the phraseology and terminology employed herein are for the purpose of description and should not be regarded as limiting.

The Junctional Tourniquet Kit is advantageous in that it involves the creation of a small multipurpose kit that can be used by the military as well as civilian medical caregivers.

Another advantage of the Junctional Tourniquet Kit is that it can be used at various locations on the torso as well as on the arms and legs.

Another advantage is to create separate parts of the Junctional Tourniquet Kit for use on specific locations on the body.

Another advantage is to create a Junctional Tourniquet Kit with a long belt that can be used in full length or be cut to various lengths for different applications.

Another advantage of the Junctional Tourniquet Kit is having the pair of utility support straps to further restrain the person from additional harmful movement and to circumvent slippage and to augment positioning of the device.

Another advantage of the Junctional Tourniquet Kit is the tourniquet belt can have a variety of combinations of hook loop attachment means on both sides.

And still another advantage of the Junctional Tourniquet Kit is an alternate embodiment of the tourniquet belt which will have a plurality of grommets on the full length and a specialized belt buckle.

A further advantage of the Junctional Tourniquet Kit is the tourniquet belt can be used in various other applications like a personal restraining belt, and a drag strap to quickly move the wounded out of harm's way.

These together with other objects of the Junctional Tourniquet Kit, along with the various features of novelty, which characterize the kit, are pointed out with particularity in the claims annexed to and forming a part of this disclosure. For a better understanding of the Junctional Tourniquet Kit, its operating advantages and the specific objects attained by its uses, reference should be made to the accompanying drawings and descriptive matter in which illustrate the preferred the embodiments.

The Junctional Tourniquet Kit consist of a tourniquet compression cam, tourniquet belt, a pressure coupler plate, a horizontal utility device, a contoured utility device, an iliac pressure device, an axillary pressure device, and a pair of utility support straps. The Junctional Tourniquet Kit will all be housed within a fabric pouch with a lanyard to thread the separate parts on keeping them together but easily accessible.

Though the Junctional Tourniquet Kit has been designed as "point specific" it can also be used to apply pressure over an occlusive dressing applied to the shoulder or at the hip in case of full arm and leg amputations. When used to apply pressure to occlusive dressings a second tourniquet is required since the first tourniquet applied would be applying pressure to the appropriate point on an artery. The application of a secondary device does not present a logistical problem since the victim AND care givers will each have their own kits and all kits contents are interchangeable. This Junctional Tourniquet Kit can also be used to secure an occlusive dressing virtually anywhere on the torso as its length allows it to be wrapped completely around the torso. The Junctional Tourniquet Kit can also be used to restrain combative casualties as is sometimes necessary in victims with severe brain injuries. This feature is also highly desirable when non-traditional vehicles are used for medical evacuations. When used as a drag/rescue strap the caregivers benefit by being able to walk/run more upright than if they were dragging the victim by the handles on the victim's plate carrier or by the boots since both means require the care giver to bend at the knees and hips.

The tourniquet cam can apply up to 4" of compression, and more if augmented. The kit allows for operator improvisations to facilitate off label applications where deemed necessary to facilitate situation specifics. The tourniquet cam is designed so that it can be used for a straight flat pull making it ideal for use as a litter strap. It can be easily coupled to additional tourniquets if the need should arise.

This tourniquet can be deployed and in place in less than 30+/− seconds; readjusted in less. It can be applied without rolling the victim around to apply it. One end is simply pushed halfway under the victim by the caregiver(s) and then pulled out the opposite side to the desired position. The tourniquet's ends are joined at the cam coupling. The cam is positioned over arteries, at compressible sites, pulled to the proper pressure (depth) and strapped down. Multiple devices can be stacked over each other without conflict as would be the case in double amputations of arms and/legs. There is nothing protruding from the tourniquet that can cause it to be dislodged or disrupted.

The Junctional Tourniquet Kit can accommodate torso diameters as small as 28 inches and as large as 60 inches.

The Junctional Tourniquet Kit is light in weight and will weigh in at approximately 12 to 32 ounces. It will be economical and available at a price far lower than the ones currently being sold. It is low cube and will fit in a pack with inside dimensions of 5" Depth×6" Width×9" Height and will be available with a container meeting USAMRMC specifications.

The heart of the Junctional Tourniquet Kit is the compression cam assembly. The tourniquet belt is connected to the cams molded in hinge shaft. It is expected that this Junctional Tourniquet Kit has an indefinite shelf life. It can be expected that military personnel will continue to encounter land mines and IED's that have been randomly scattered in unstable countries as well and that pose a definite threat to their well-being.

Since the detonation of mines, and IEDs, frequently involve multiple casualties and amputations it is recommended that all military personnel, in theaters of operation, have a Junctional Tourniquet Kit in addition to their IFAK. Forward combat medical personnel will then have their own kit, as well as the casualty's kit, resulting in the medical corpsman equipped to deal with double extremity amputations.

Civilian law enforcement would also benefit by having their personnel carry Junctional Tourniquet for situations like the Boston Marathon attacks.

With respect to the above description then, it is to be realized that the optimum dimensional relationships for the parts of the Junctional Tourniquet Kit, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present design. Therefore, the foregoing is considered as illustrative only of the principles of the Junctional Tourniquet Kit. Further, since numerous modifications and changes will readily occur to those skilled in the art, it is not desired to limit the design to the exact construction and operation shown and described, and accordingly, all suitable modifications and equivalents may be resorted to, falling within the scope of the invention.

BRIEF DESCRIPTION OF THE DRAWINGS

The accompanying drawings, which are incorporated in and form a part of this specification, illustrate embodiments of the Junctional Tourniquet Kit and together with the description, serve to explain the principles of this application.

FIG. 1 a front view of the major components of the Junctional Tourniquet Kit.

FIG. 2 depicts an end view of the tourniquet compression cam and belt pressing down on the pressure coupler plate and the horizontal utility device compressing a typical artery.

FIG. 8 depicts a segment of the tourniquet belt with hook sections on either side and a loop section down the center.

FIG. 9 depicts a segment of the tourniquet belt with loop sections on both sides and hook section down the center.

FIG. 10 depicts a segment of the tourniquet belt with hook and loop segments on an angle.

FIG. 11 depicts a segment of the tourniquet belt with plurality of grommets on the full length.

FIG. 12 depicts a perspective view of an alternate embodiment of a tourniquet belt with a plurality of grommets on the full length and a specialized belt buckle.

Figure 3:
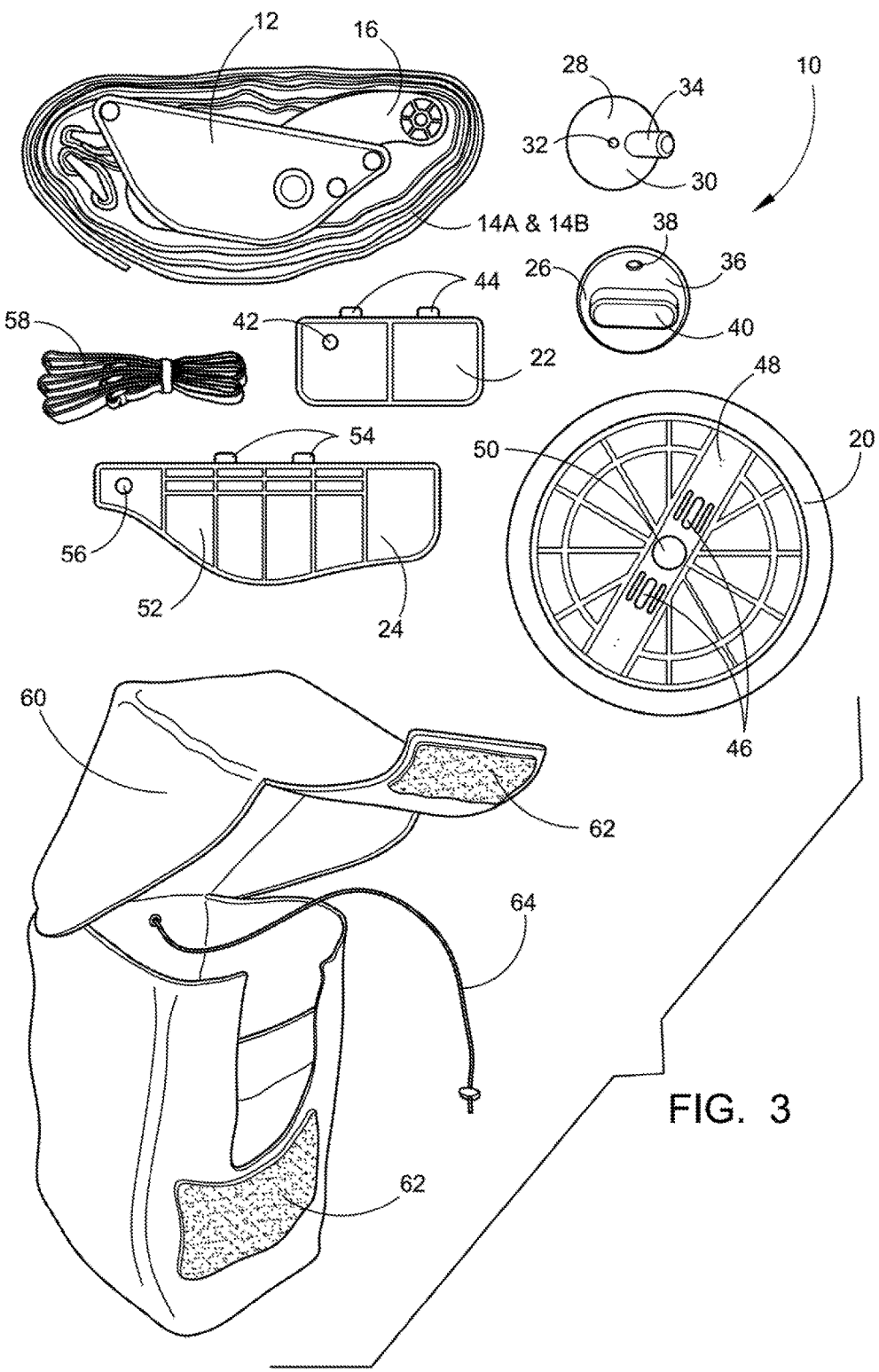
FIG. 3 depicts all of the components of the Junctional Tourniquet Kit.

The Junctional Tourniquet Kit consist of a tourniquet compression cam, tourniquet belt, a pressure coupler plate, a horizontal utility device, a contoured utility device, an iliac pressure device, an axillary pressure device, and a pair of utility support straps. The Junctional Tourniquet Kit will all be housed within a fabric pouch with a lanyard to thread the separate parts on keeping them together but easily accessible.

DETAILED DESCRIPTION OF THE PREFERRED EMBODIMENTS

Referring now to the drawings, wherein similar parts of the Junctional Tourniquet Kit 10 identified by like reference numerals, there is seen in FIG. 1 a front view of some of the components of the Junctional Tourniquet Kit 10 and the actions of the tourniquet compression cam 12 along with the associated parts of the kit. The tourniquet compression cam 12 can be used as a compression device to restrict the flow of blood through an artery or it can be used as a means to tighten the tourniquet belt 14A into a desired position.

The tourniquet compression cam 12 is shown with a short section of the tourniquet belt 14A attached around the upper section of the cam lever 16 by a hook-loop attachment means 18. A long section of the tourniquet belt 14B is attached around the left side of the tourniquet compression cam 12 by a second hook-loop attachment means 18 to be extended around the person and pulled tight to the right side of the tourniquet compression cam 12 and secured to it by a third hook-loop attachment means 18. The short section of the tourniquet belt 14A is then pulled, rotating the upper section of the cam lever arm 16 and extending the lower section of the cam lever 16 downward. The short section of the tourniquet belt 14A is then secured to the long section of the tourniquet belt 14B by the fourth hook-loop attachment means 18. The belts 14A and 14B will have a hook-loop attachment means 18 on both sides.

The pressure coupler plate 20 is shown below the tourniquet compression cam 12 to be attached to the horizontal utility point specific pressure device 22, or the contoured utility point specific pressure device 24, or the iliac point specific pressure device 26 when a specific tourniquet application is needed.

FIG. 2 depicts an end view of the tourniquet compression cam 12 and tourniquet belt pressing down on the pressure coupler plate 20 and the horizontal utility device compressing a typical artery.

FIG. 3 depicts all of the components of the Junctional Tourniquet Kit 10 including the tourniquet compression cam 12 having a cam lever 16, the tourniquet belt 14A and 14B, the axillary device 28 with a flat base 30, a lanyard orifice 32, and pinpoint angled dowel 34 for centralized pressure positioning. Additional parts to the kit include the iliac pressure device 26 having a flat base 36, a lanyard orifice 38 and an elongated pressure section 40. A horizontal utility device 22 with a lanyard orifice 42 has two key elements 44 that locate within orifices 46 in the alignment track 48 on the pressure coupler plate 20. The pressure coupler plate 20 has a central lanyard orifice 50. The contoured utility device 52 with the two key elements 54 that locate within orifices 46 in the alignment track 48 on the pressure coupler plate 20 and a lanyard orifice 56. The contoured utility device 52 has been designed to fit into the variety of contours in the hip area. A set of utility support or restraint straps 58 are included within the kit. The complete Junctional Tourniquet Kit 10 will fit into the fabric kit bag 60 having the hook-loop closure sections 62 and the attached lanyard 64. This specific point junctional tourniquet kit is expandable in that components of one can be added to another to address numerous unique issues when encountered in the field.

Figures 4, 5:
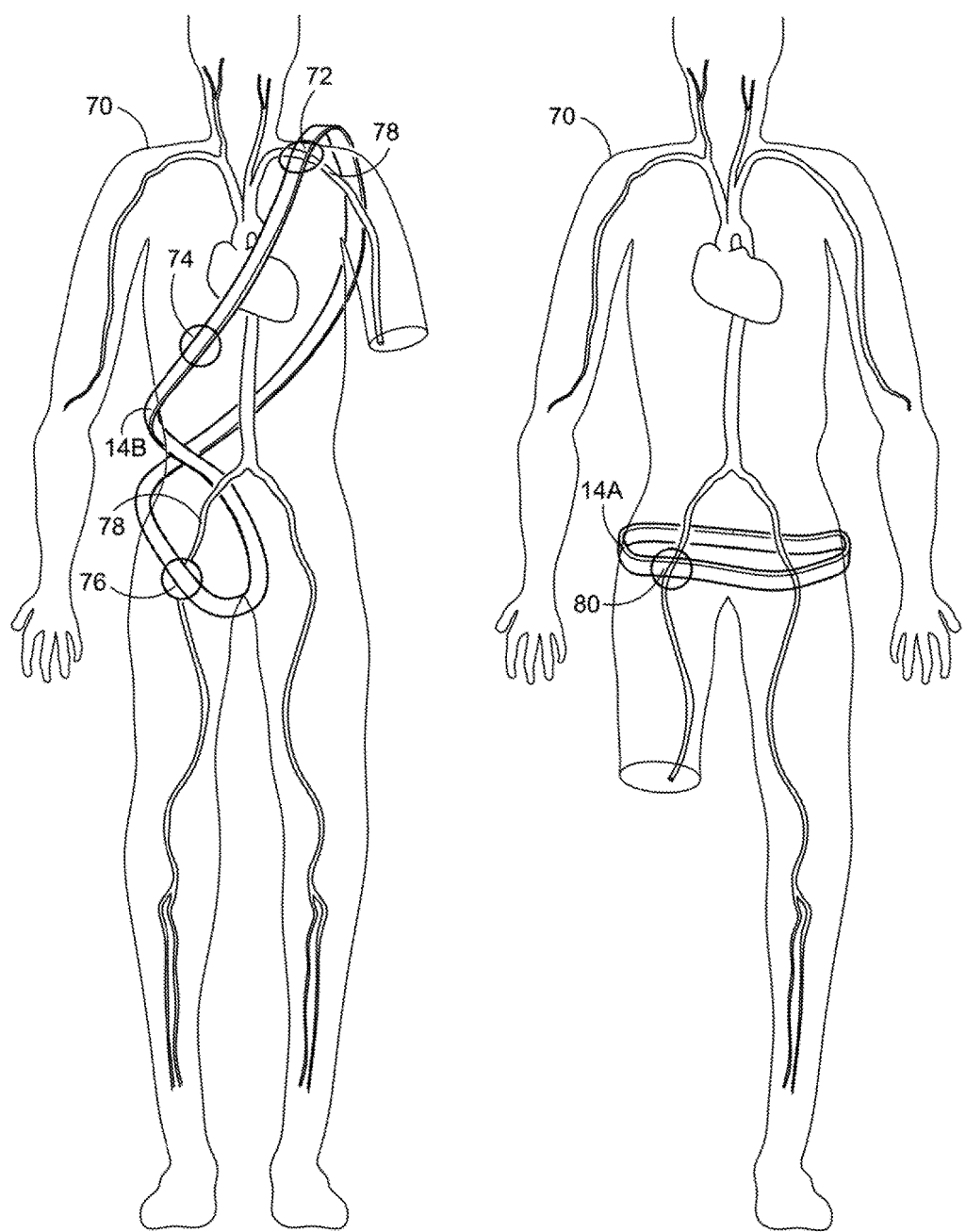
FIG. 4 depicts a silhouette of a person with the tourniquet belt wrapped around indicating some the locations that the pressure may be applied on the major arteries on one side of the body.
FIG. 5 depicts a silhouette of a person with the tourniquet belt wrapped around the lower waist of the person.

FIG. 4 depicts a silhouette of a person 70 with the tourniquet belt 14B wrapped around indicating some the pressure locations 72, 74 and 76 that the pressure may be applied on the major arteries 78 on one side of the body. The tourniquet belt strap could also be used to fashion/fabricate an improvised splint, and maybe even a soft cast as a result of the configuration of the hook and loop sewn onto the strap.

FIG. 5 depicts a silhouette of a person 70 with the tourniquet belt 14A wrapped around the lower waist of the person indicating a pressure location 80 on one side of the body. This tourniquet belt 14A could also be used to stabilize flailed chests, flailed hips and or flailed shoulders if necessary.

Figures 6, 7:
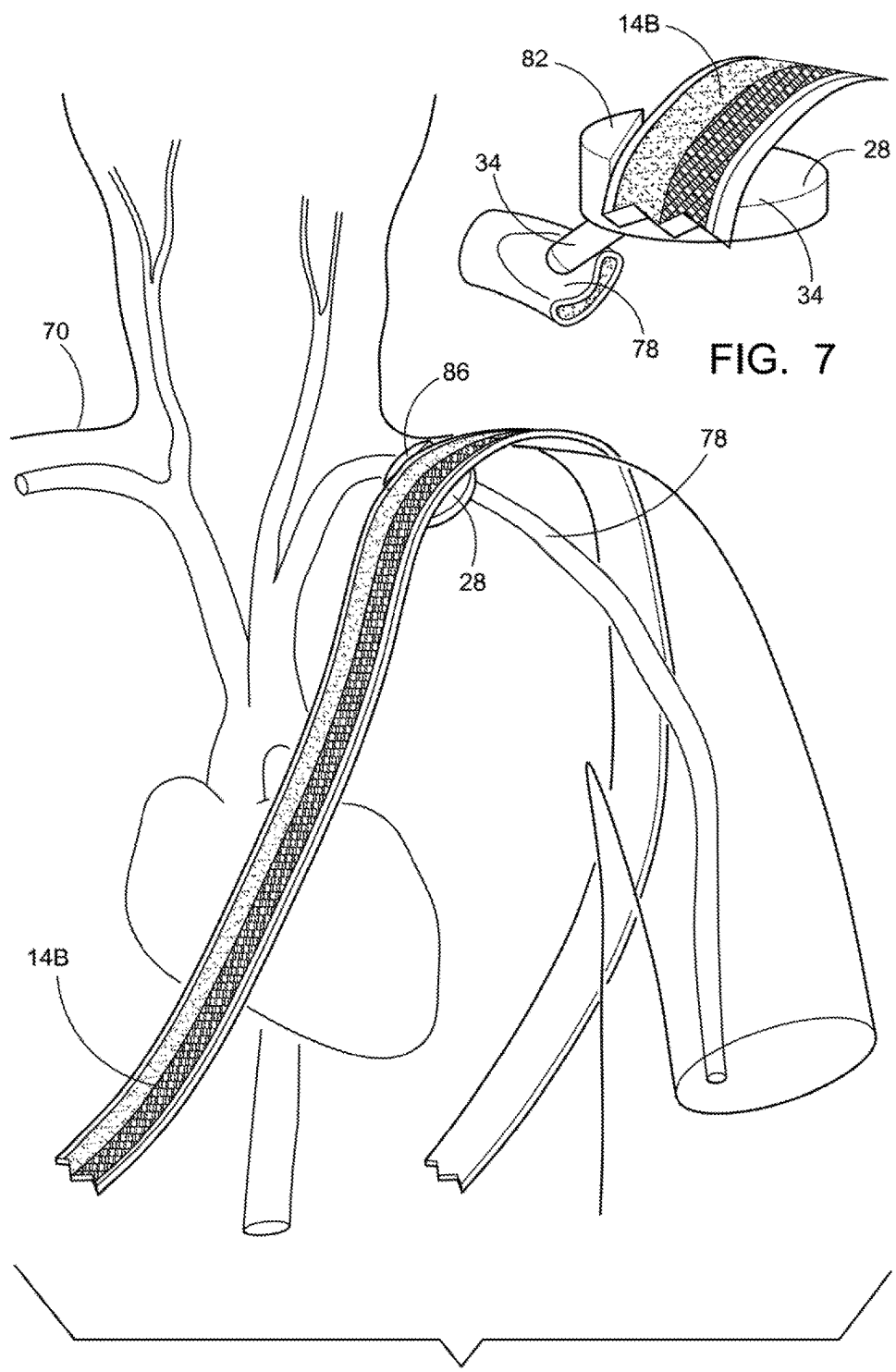
FIG. 6 depicts an enlarged silhouette of the shoulder area with the tourniquet belt going over the axillary pressure device.
FIG. 7 depicts a perspective illustration of the tourniquet belt over the axillary pressure device putting pressure on an artery.

FIG. 6 depicts an enlarged silhouette of the shoulder area of a person 70 with the tourniquet belt 14B having a strip of hook material and a strip of loop material together going over the axillary pressure device 28 with the retainer edge 82 keeping the tourniquet belt 14B in position. With the strips of hook material and loop material on both sides of the tourniquet belt 14B the belt can be turned over to secure it together into position. In this application the tourniquet compression cam 12 could be used as a means to tighten the tourniquet belt 14B into the desired location.

FIG. 7 depicts a perspective illustration of the tourniquet belt 14B over the axillary pressure device 28 with the angled dowel 34 putting direct pressure on an major artery 78 with the tourniquet belt 14B held in position by the means of the retainer edge 82.

FIG. 8 depicts a segment of the tourniquet belt 14C with hook sections on the outside and loop section down the center.

FIG. 9 depicts a segment of the tourniquet belt 14D with loop sections on the outside and hook sections down the center.

FIG. 10 depicts a segment of the tourniquet belt 14E with hook and loop segments on an angle.

FIG. 11 depicts a segment of the tourniquet belt 14F with plurality of grommets 88 on the full length.

FIG. 12 depicts a perspective view of an alternate embodiment of a tourniquet belt 14F with a plurality of grommets 88 on the full length and a specialized belt buckle 90.

Figure 13:
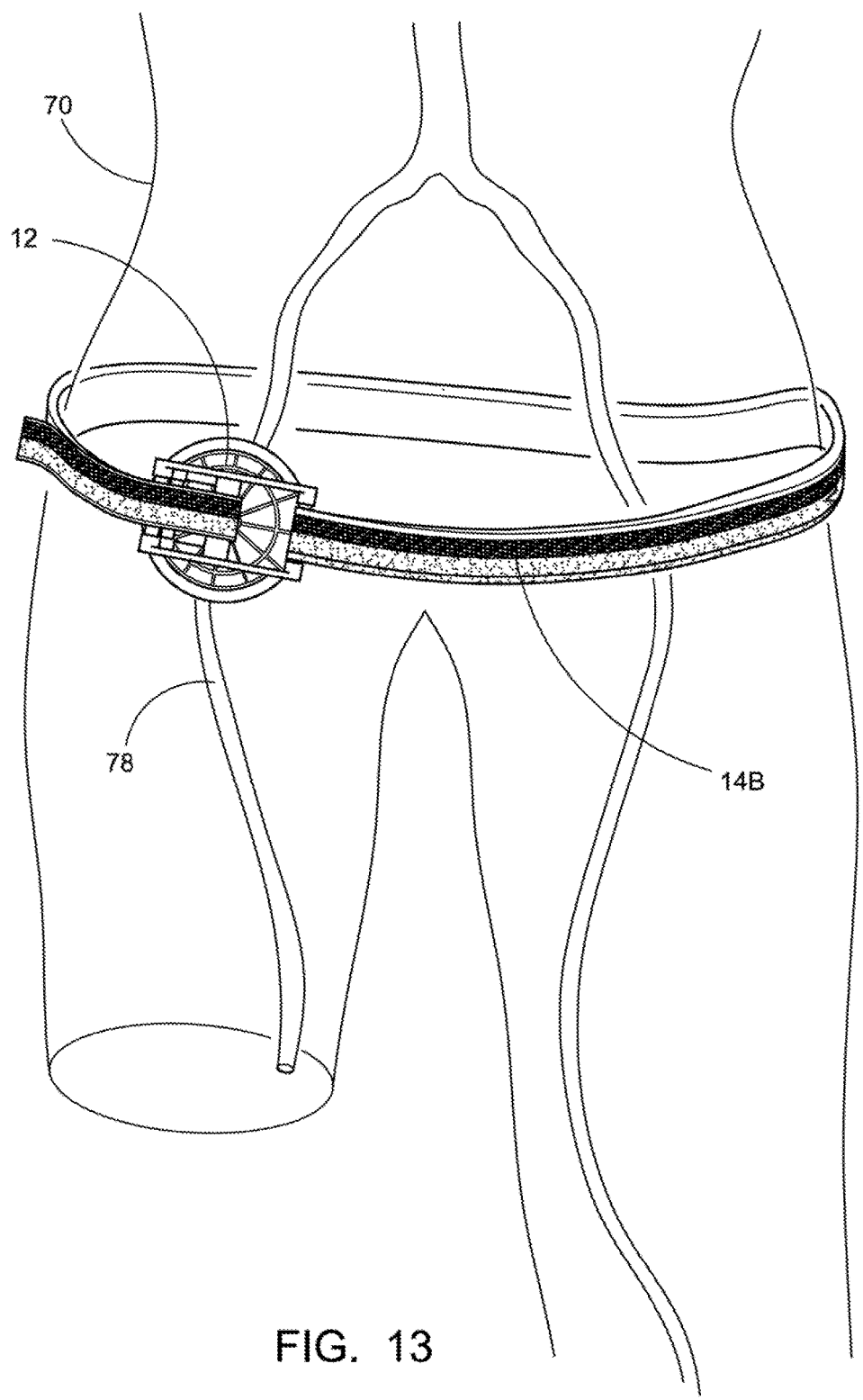
FIG. 13 depicts a silhouette of the lower portion of a person with the tourniquet compression cam and tourniquet belt putting pressure on the right iliac artery.

FIG. 13 depicts a silhouette of the lower portion of a person 70 with the tourniquet compression cam 12 and tourniquet belt 14B putting pressure on the major artery 78.

Figures 14, 15:
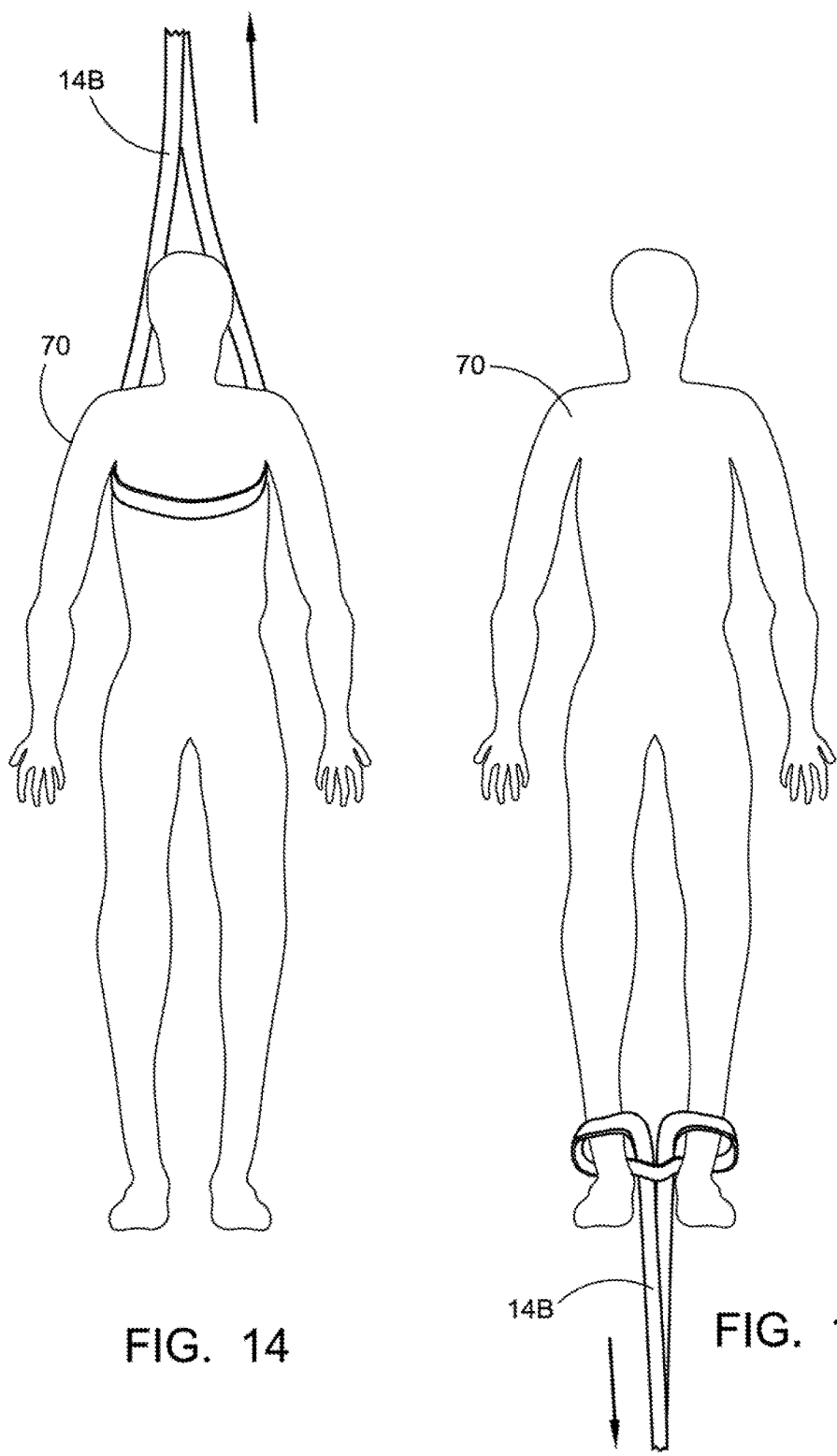
FIG. 14 depicts silhouette of a person with the tourniquet belt being used as a drag strap under the arms.
FIG. 15 depicts silhouette of a person with the tourniquet belt being used as a drag strap around the ankles.

FIG. 14 depicts silhouette of a person 70 with the tourniquet belt 14B being used as a drag strap under the arms.

FIG. 15 depicts silhouette of a person 70 with the tourniquet belt 14B being used as a drag strap around the ankles.

The Junctional Tourniquet Kit 10 shown in the drawings and described in detail herein disclose arrangements of elements of particular construction and configuration for illustrating preferred embodiments of structure and method of operation of the present design. It is to be understood, however, that elements of different construction and configuration and other arrangements thereof, other than those illustrated and described may be employed for providing a Junctional Tourniquet Kit 10 in accordance with the spirit of this application, and such changes, alternations and modifications as would occur to those skilled in the art are considered to be within the scope of this application as broadly defined in the appended claims.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the Junctional Tourniquet Kit of the application, which is measured by the claims, nor is it intended to be limiting as to the scope of the design in any way.

I claim:

1. A point specific junctional tourniquet kit comprising:
   (a) a tourniquet compression cam including a housing having a left side and a right side, wherein said tourniquet compression cam includes a cam lever having an upper section and a lower section, and further wherein said cam lever is rotatably attached to said housing;
   (b) a tourniquet compression cam belt further including a short section tourniquet belt attached to said upper section of said cam lever and a long section tourniquet belt attached around the left side of the tourniquet compression cam housing, wherein when said short section tourniquet belt is pulled to the right said cam lever rotates extending said lower section of said cam lever downward: and
   (c) an attachment mechanism portion located on said short section tourniquet belt and said long section tourniquet belt of said tourniquet compression cam belt; and
   (d) a pressure coupler plate and a plurality of point specific pressure devices; wherein when said tourniquet compression cam is applied, and said short and long section tourniquet belts are pulled tight, said cam lever rotates within said housing and extends outward from said housing to apply pressure on the pressure coupler plate which in turn transfers pressure to a coupled point specific pressure device, thereby applying increasing pressure to a wound, and can then be secured using said attachment mechanism portion.

2. The point specific junctional tourniquet kit according to claim 1, further including said pressure coupler plate and said plurality of point specific pressure devices, wherein said tourniquet compression cam is configured to removably attach to said pressure coupler plate.

3. The point specific junctional tourniquet kit according to claim 2, wherein said pressure coupler plate is configured to removably and replaceably mount one of said point specific pressure devices.

4. The point specific junctional tourniquet kit according to claim 3, wherein said point specific pressure device includes a horizontal point specific pressure device.

5. The point specific junctional tourniquet kit according to claim 3, wherein said point specific pressure device includes a contoured point specific pressure device.

6. The point specific junctional tourniquet kit according to claim 3, wherein said point specific pressure device includes an iliac point specific pressure device.

7. The point specific junctional tourniquet kit according to claim 3, wherein said point specific pressure device includes an axillary point specific pressure device.

8. The point specific junctional tourniquet kit according to claim 1, wherein said attachment mechanism portion located on said short section tourniquet belt and said long section tourniquet belt of said tourniquet compression cam belt includes a hook and loop fastener in varying patterns to secure said tourniquet compression cam belt.

9. The point specific junctional tourniquet kit according to claim 1, wherein said attachment mechanism portion located on said short section tourniquet belt and said long section tourniquet belt of said tourniquet compression cam belt includes a plurality of grommets and a belt buckle accepting said plurality of grommets as a fastener to secure said tourniquet compression cam belt.

10. The point specific junctional tourniquet kit according to claim 1, wherein said kit includes said tourniquet compression cam attached to said short section tourniquet belt and said long section tourniquet belt, said pressure coupler plate, a horizontal point specific pressure device, a contoured point specific pressure device, an iliac point specific pressure device and an axillary point specific pressure device, and a set of restraint straps all contained within a kit bag for rapid deployment.

11. A method for making a point specific junctional tourniquet kit comprising the steps of:
    (a) providing a tourniquet compression cam including a housing having a left side and a right side, wherein said tourniquet compression cam includes a cam lever having an upper section and a lower section, and further wherein said cam lever is rotatably attached to said housing;
    (b) providing a tourniquet compression cam belt further including a short section tourniquet belt attached to said upper section of said cam lever and a long section tourniquet belt attached around the left side of the tourniquet compression cam housing, wherein when said short section tourniquet belt is pulled to the right said cam lever rotates extending said lower section of said cam lever;
    (c) providing an attachment mechanism portion located on said short section tourniquet belt and said long section tourniquet belt of said tourniquet compression cam belt;
    (d) providing a pressure coupler plate and a plurality of point specific pressure devices attachable to said pressure coupler plate; and
    (e) providing a lanyard attached to said plurality of compression devices attachable to said flat base, and a carry bag for containment of all junctional tourniquet kit components:
    wherein when said tourniquet compression cam is applied, and said short and long section tourniquet belts are pulled tight, said cam lever rotates within said housing and extends outward from said housing to apply pressure on the pressure coupler plate which in turn transfers pressure to a coupled point specific pressure device, thereby applying increasing pressure to put a wound, and can then be secured using said attachment mechanism portion.

12. The method for making a point specific junctional tourniquet kit according to claim 11, further including said pressure coupler plate and said plurality of point specific pressure devices, wherein said tourniquet compression cam is configured to removably attach to said pressure coupler plate.

13. The method for making a point specific junctional tourniquet kit according to claim 12, wherein pressure coupler plate is configured to removably and replaceably mount one of said point specific pressure devices.

14. The method for making a point specific junctional tourniquet kit according to claim 13, wherein said point specific pressure device includes a horizontal point specific pressure device.

15. The method for making a point specific junctional tourniquet kit according to claim 13, wherein said point specific pressure device includes a contoured point specific pressure device.

16. The method for making a point specific junctional tourniquet kit according to claim 13, wherein said point specific pressure device includes an iliac point specific pressure device.

17. The method for making a point specific junctional tourniquet kit according to claim 13, wherein said point specific pressure device includes an axillary point specific pressure device.

18. The method for making a point specific junctional tourniquet kit according to claim 11, wherein said attachment mechanism portion located on said short section tourniquet belt and said long section tourniquet belt of said tourniquet compression cam belt includes a hook and loop fastener in varying patterns to secure said tourniquet compression cam belt.

19. The method for making a point specific junctional tourniquet kit according to claim 11, wherein said attachment mechanism portion located on said short section tourniquet belt and said long section tourniquet belt of said tourniquet compression cam belt includes a plurality of grommets and a belt buckle accepting said plurality of grommets as a fastener to secure said tourniquet compression cam belt.

20. The method for making a point specific junctional tourniquet kit according to claim 11, wherein said kit includes said tourniquet compression cam attached to said short section tourniquet belt and said long section tourniquet belt, said pressure coupler plate, a horizontal point specific pressure device, a contoured point specific pressure device, an iliac point specific pressure device and an axillary point specific pressure device, and a set of restraint straps all contained within a kit bag for rapid deployment.

\* \* \* \* \*